US006898530B1

(12) United States Patent
Saffer et al.

(10) Patent No.: US 6,898,530 B1
(45) Date of Patent: May 24, 2005

(54) METHOD AND APPARATUS FOR EXTRACTING ATTRIBUTES FROM SEQUENCE STRINGS AND BIOPOLYMER MATERIAL

(75) Inventors: Jeffrey D. Saffer, Richland, WA (US); Augustin J. Calapristi, West Richland, WA (US); Nancy E. Miller, San Diego, CA (US); Randall E. Scarberry, Richland, WA (US); Heidi J. Sofia, Walla Walla, WA (US); Lisa C. Stillwell, Richland, WA (US); Guang Chen, Richland, WA (US); Philip J. Monroe, Johnstown, OH (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/409,260

(22) Filed: Sep. 30, 1999

(51) Int. Cl.[7] .......................... G01N 33/48; G01N 31/00
(52) U.S. Cl. .......................................... 702/19; 702/20
(58) Field of Search ..................................... 702/20, 19

(56) References Cited

U.S. PATENT DOCUMENTS

| | | | |
|---|---|---|---|
| 5,047,842 A | 9/1991 | Bouman, Jr. et al. ......... 358/75 |
| 5,121,337 A | 6/1992 | Brown ....................... 364/498 |
| 5,325,298 A | 6/1994 | Gallant .................. 364/419.19 |
| 5,361,326 A | 11/1994 | Aparicio, IV et al. ........ 395/21 |
| 5,446,681 A | 8/1995 | Gethner et al. ............. 364/554 |
| 5,506,937 A | 4/1996 | Ford et al. .................... 395/12 |
| 5,528,735 A | 6/1996 | Strasnick et al. ........... 395/127 |
| 5,546,472 A | 8/1996 | Levin ......................... 382/131 |
| 5,555,354 A | 9/1996 | Strasnick et al. ........... 395/127 |
| 5,592,599 A | 1/1997 | Lindholm ................... 345/427 |
| 5,619,709 A | 4/1997 | Caid et al. .................. 395/794 |
| 5,623,679 A | 4/1997 | Rivette et al. .............. 395/773 |
| 5,623,681 A | 4/1997 | Rivette et al. .............. 395/788 |
| 5,625,767 A | 4/1997 | Bartell et al. ............... 395/140 |
| 5,659,766 A | 8/1997 | Saund et al. ................ 395/759 |
| 5,671,381 A | 9/1997 | Strasnick et al. ........... 395/355 |
| 5,675,788 A | 10/1997 | Husick et al. .............. 395/615 |
| 5,687,364 A | 11/1997 | Saund et al. ................ 395/605 |
| 5,692,107 A | 11/1997 | Simoudis et al. ............. 395/50 |
| 5,696,963 A | 12/1997 | Ahn ........................... 395/605 |
| 5,699,507 A | 12/1997 | Goodnow, II et al. .. 395/183.14 |
| 5,721,903 A | 2/1998 | Anand et al. ............... 395/605 |
| 5,721,912 A | 2/1998 | Stepczyk et al. ........... 395/613 |
| 5,732,260 A | 3/1998 | Nomiyama ................. 395/605 |
| 5,737,591 A | 4/1998 | Kaplan et al. .............. 395/601 |
| 5,751,612 A | 5/1998 | Donovan et al. ........... 364/578 |
| 5,767,854 A | 6/1998 | Anwar ....................... 345/355 |
| 5,784,544 A | 7/1998 | Stevens ...................... 395/605 |
| 5,787,274 A | 7/1998 | Agrawal et al. ............ 395/613 |
| 5,794,178 A | 8/1998 | Caid et al. ...................... 704/9 |
| 5,819,258 A | 10/1998 | Vaithyanathan et al. ....... 707/2 |
| 5,838,973 A | 11/1998 | Carpenter-Smith et al. . 395/701 |
| 5,842,206 A | 11/1998 | Sotomayor ................... 707/5 |
| 5,857,179 A | 1/1999 | Vaithyanathan et al. ....... 707/2 |
| 5,857,185 A | 1/1999 | Yamaura ....................... 707/5 |
| 5,861,891 A | 1/1999 | Becker ....................... 345/433 |
| 5,864,863 A | 1/1999 | Burrows ..................... 707/103 |
| 5,873,076 A | 2/1999 | Barr et al. ..................... 707/3 |
| 5,907,838 A | 5/1999 | Miyasaka et al. .............. 707/4 |
| 5,913,214 A | 6/1999 | Madnick et al. ............. 707/10 |
| 5,918,010 A | 6/1999 | Appleman et al. ..... 395/200.33 |
| 5,926,806 A | 7/1999 | Marshall et al. ............... 707/3 |
| 5,926,820 A | 7/1999 | Agrawal et al. ............ 707/200 |
| 5,930,784 A | 7/1999 | Hendrickson ................. 707/2 |
| 5,930,803 A | 7/1999 | Becker et al. .............. 707/104 |
| 5,945,982 A | 8/1999 | Higashio et al. ............ 345/203 |
| 5,953,006 A | 9/1999 | Baker et al. ................ 345/326 |
| 5,953,716 A | 9/1999 | Madnick et al. ............... 707/4 |
| 5,963,965 A | 10/1999 | Vogel ......................... 707/501 |
| 5,966,139 A | 10/1999 | Anupam et al. ............ 345/440 |
| 5,982,370 A | 11/1999 | Kamper ..................... 345/356 |
| 5,986,652 A | 11/1999 | Medl et al. ................. 345/339 |
| 5,986,673 A | 11/1999 | Martz ......................... 345/440 |
| 5,987,470 A | 11/1999 | Meyers et al. .............. 707/102 |
| 5,991,714 A | 11/1999 | Shaner .......................... 704/9 |
| 5,999,192 A | 12/1999 | Selfridge et al. ........... 345/440 |
| 5,999,937 A | 12/1999 | Ellard ........................ 707/101 |
| 6,012,053 A | 1/2000 | Pant et al. ..................... 707/3 |
| 6,014,661 A | 1/2000 | Ahlberg et al. ................ 707/3 |
| 6,023,694 A | 2/2000 | Kouchi et al. ................. 707/2 |
| 6,026,409 A | 2/2000 | Blumenthal ................ 707/104 |

(Continued)

FOREIGN PATENT DOCUMENTS

| | | | | |
|---|---|---|---|---|
| EP | 0 202 686 A2 | 11/1986 | ........... | G06F/15/72 |
| EP | 0 627 692 A1 | 7/1994 | ......... | G06F/15/403 |
| EP | 0 717 346 A2 | 6/1996 | ........... | G06F/3/033 |
| WO | WO99/27495 | 6/1999 | ........... | G06T/11/00 |

OTHER PUBLICATIONS

Altschul et al. Basic Local Alignment Search Tool. 1990. Journal of Molecular Biology. vol. 215, pp. 403–410.*
Higgins, Desmond G., "Sequence ordinations: a multivariate analysis approach to analyzing large sequence data sets," *Comput. Appl. Biosc.*, vol. 8, 1992, pp. 15–22.
"Screening Cheminformatics Data", visited at http://www-.partek.com/chem/screen.html on Apr. 15, 1999, 2 pages.

(Continued)

*Primary Examiner*—Marianne P. Allen
*Assistant Examiner*—Channing S. Mahatan
(74) *Attorney, Agent, or Firm*—Finnegan, Henderson, Farabow, Garrett & Dunner, L.L.P.; Konstantin M. Linnik

(57) ABSTRACT

Systems for creating high-dimensional vectors representing sequence strings and biopolymer materials are provided. A first system for divides respective sequence strings into blocks of at least three units to create a vocabulary of blocks. A second system selects predefined domains of a plurality of items of biopolymer materials. A third system defines each item of biopolymer material in a data set of biopolymer materials as a surface using descriptors of at least one of structure and function. A fourth system compares information regarding each biopolymer material of a plurality of biopolymer materials to information regarding each other biopolymer material.

10 Claims, 7 Drawing Sheets

U.S. PATENT DOCUMENTS

| | | | |
|---|---|---|---|
| 6,029,176 A | 2/2000 | Cannon | 707/104 |
| 6,032,157 A | 2/2000 | Tamano et al. | 707/104 |
| 6,034,697 A | 3/2000 | Becker | 345/433 |
| 6,035,057 A | 3/2000 | Hoffman | 382/159 |
| 6,038,538 A | 3/2000 | Agrawal et al. | 705/7 |
| 6,038,561 A | 3/2000 | Snyder et al. | 707/6 |
| 6,044,366 A | 3/2000 | Graffe et al. | 707/2 |
| 6,049,806 A | 4/2000 | Crecine | 707/200 |
| 6,058,391 A | 5/2000 | Gardner | 707/4 |
| 6,067,542 A | 5/2000 | Carino, Jr. | 707/4 |
| 6,073,115 A | 6/2000 | Marshall | 705/35 |
| 6,073,138 A | 6/2000 | de l'Etraz et al. | 707/104 |
| 6,078,314 A | 6/2000 | Ahn | 345/169 |
| 6,078,914 A | 6/2000 | Redfern | 707/3 |
| 6,081,788 A | 6/2000 | Appleman et al. | 705/14 |
| 6,081,802 A | 6/2000 | Atherton et al. | 707/3 |
| 6,085,190 A | 7/2000 | Sakata | 707/6 |
| 6,088,032 A | 7/2000 | Mackinlay | 345/355 |
| 6,092,061 A | 7/2000 | Choy | 707/1 |
| 6,094,648 A | 7/2000 | Aalbersberg | 707/3 |
| 6,094,649 A | 7/2000 | Bowen et al. | 707/3 |
| 6,098,065 A | 8/2000 | Skillen et al. | 707/3 |
| 6,100,901 A | 8/2000 | Mohda et al. | 345/440 |
| 6,101,493 A | 8/2000 | Marshall et al. | 707/3 |
| 6,108,004 A | 8/2000 | Medl | 345/346 |
| 6,108,651 A | 8/2000 | Guha | 707/4 |
| 6,108,666 A | 8/2000 | Floratos et al. | 707/104 |
| 6,111,578 A | 8/2000 | Tesler | 345/356 |
| 6,112,194 A | 8/2000 | Bigus | 706/11 |
| 6,112,209 A | 8/2000 | Gusack | 707/101 |
| 6,121,969 A | 9/2000 | Jain et al. | 345/355 |
| 6,122,636 A | 9/2000 | Malloy et al. | 707/102 |
| 6,128,624 A | 10/2000 | Papierniak et al. | 707/104 |
| 6,252,597 B1 | 6/2001 | Lokuge | 345/353 |
| 6,259,451 B1 | 7/2001 | Tesler | 345/419 |
| 6,289,353 B1 | 9/2001 | Hazlehurst et al. | 707/102 |
| 6,327,574 B1 | 12/2001 | Kramer et al. | 705/14 |
| 6,484,168 B1 | 11/2002 | Pennock et al. | 707/6 |
| 6,493,709 B1 | 12/2002 | Aiken | 707/4 |

OTHER PUBLICATIONS

"Variable Transformation", visited at http://www.partek.com/chem/tx.html on Apr. 15, 1999, 1 page.

"Visualization of High Dimensional Data", Visited at http://www.partek.com/chem/viz.html on Apr. 15, 1999, 3 page.

"Correlating Activities w/Structural Descriptors", visited at http://www.partek.com/chem/cor.html on Apr. 15, 1999, 6 pages.

"Cluster Analysis of Cheminformatics Data", visited at http://www.partek.com/chem/cla.html on Apr. 15, 1999, 2 pages.

Cleveland, William S., *Visualizing Data*, Hobart Press, Summit, New Jersey, 1993, pp. 1–360.

Nielson, Gregory M. et al., *Scientific Visualization*, IEEE Computer Society, 1997, pp. 1–577.

Hobohm, Uwe et al., "A Sequence Property Approach to Searching Protein Databases", *Journal of Molecular Biology*, 1995, pp. 390–399.

van Heel, Martin, "A New Family to Powerful Multivariate Statistical Sequence Analysis Techniques", *Journal of Molecular Biology*, 1991, pp. 877–887.

Becker, Richard A. et al., "Brushing Scatterplots", *Technometrics*, May 1987, vol. 29, No. 2, pp. 127–142.

Agrafiotis, Dimitris K., "A New Method for Analyzing Protein Sequence Relatsionships Based on Sammon Maps", *Protein Science*, vol. 6, 1997, pp. 287–293.

Eisen, Michael B. et al., "Cluster Analysis and Display of Genome–Wide Expression Patterns," *Proc. Nat'l Acad. Sci., USA*, vol. 95, 1998, pp. 14863–14868.

"Silicon Graphics MineSet™, Supporting the Discovery Research Process," *MineSet for Discovery Research*, Spring 1999, pp. 1–49.

"Spotfire Pro 4.0—Speeding Discovery", visited at http://www.sportfire.com/of_2_1.htm on Jun. 17, 1999, 2 pages.

"Spotfire Pro—Offerings—Spotfire", visited at http://www.spotfire.com/of on Jun. 17, 1999, 2 pages.

"Discovery Innovation—Spotfire", visited at http://www.spotfire.com/di_1_1.htm. on Jun. 17, 1999, 1 page.

"Discovery Innovation—Spotfire", visited at http://www.spotfire.com/di_1_1_4.htm on Jun. 17, 1999, 1 page.

"Downloads—Spotfire", visited at http://www.spotfire.com/down_00.htm#2.1.2 on Jun. 17, 1999, 1 page.

"Offerings—Spotfire", visited at http://www.spotfire.com/of_2_4.htm on Jun. 17, 1999, 1 page.

"Partners—Spotfire", visited at http://www.spotfire.com/pa_4_0.htm on Jun. 17, 1999, 2 pages.

"Partners—Spotfire", visited at http://www.spotfire.com/pa_4_2.htm on Jun. 17, 1999, 1 page.

"Cheminformatics Example", visited at http://www.partek.com/chem/index,html on Apr. 15, 1999, 1 page.

"Cheminformatics Data Description", visited at http://www.partek.com/chem/data,html on Apr. 15, 1999, 1 page.

"Predicting Mechanism of Action from Activity Patterns", visited at http://www.partek.com/chem/mtp.html on Apr. 15, 1999, 3 pages.

U.S. Appl. No. 09/408,716– Nancy Miller et al., —filed Sep. 30, 1999.

U.S. Appl. No. 09/410,367—Jeffrey Saffer et al.—filed Sep. 30, 1999.

Bertin, Jacques, *Semiology of Graphics*, University of Wisconsin Press, 1983.

* cited by examiner

SEQUENCE LISTING

<160> NUMBER OF SEQ ID NOS: 3

<210> SEQ ID NO 1
<211> LENGTH: 10
<212> TYPE: DNA

-continued

```
<213> ORGANISM: Artificial Sequence
<220> FEATURE:
<223> OTHER INFORMATION: Description of Artificial Sequence:  Artificial
      sequence to exemplify typical notations used to describe
      sequences.

<400> SEQUENCE: 1
gattctagga                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:  Artificial
      sequence to exemplify typical notations used to describe
      sequences.
<220> FEATURE:
<221> NAME/KEY: misc_RNA
<222> LOCATION: (2)
<223> OTHER INFORMATION: T represents uracil in this RNA
<220> FEATURE:
<221> NAME/KEY: misc_RNA
<222> LOCATION: (9)
<223> OTHER INFORMATION: T represents uracil in this RNA

<400> SEQUENCE: 2
atggaccata                                                            10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Artificial
      sequence to exemplify typical notations used to describe
      sequences.

<400> SEQUENCE: 3

Met Arg Lys Leu Ala Gly Gln Pro Ser
 1               5
```

METHOD AND APPARATUS FOR EXTRACTING ATTRIBUTES FROM SEQUENCE STRINGS AND BIOPOLYMER MATERIAL

RELATED APPLICATIONS

The following identified U.S. patent applications are relied upon and are incorporated by reference in their entirety in this application:

U.S. patent application Ser. No. 08/695,455, entitled "THREE-DIMENSIONAL DISPLAY OF DOCUMENT SET," filed on Aug. 12, 1996;

U.S. patent application Ser. No. 08/713,313, entitled "SYSTEM FOR INFORMATION DISCOVERY," filed on Sep. 13, 1996;

U.S. patent application Ser. No. 09/408,716, entitled "METHODS AND APPARATUS FOR DISPLAYING DISPARATE TYPES OF INFORMATION USING AN INTERACTIVE SURFACE MAP," filed on the same date herewith by Jeffrey Saffer, et al.; and U.S. patent application Ser. No. 09/410,367, entitled "DATA PROCESSING, ANALYSIS, AND VISUALIZATION SYSTEM FOR USE WITH DISPARATE DATA TYPES," filed on the same date herewith by Jeffrey Saffer, et al.

BACKGROUND OF THE INVENTION

A. Field of the Invention

The present invention relates to extracting attributes from sequence strings and from information representing biopolymer materials, and more particularly to a method and apparatus which extracts attributes from information representing biopolymer material to create objects useful for analyzing large amounts of data using multivariate analysis.

B. Description of the Related Art

DNA, RNA, and proteins represent key functional units in biological systems. DNA is composed of nucleotide subunits (deoxyadenosine, deoxythymidine, deoxycytidine, and deoxyguanosine) linked together to form an array of biopolymer material. Often, the linked chain is bound to a complementary chain to form a double helix. The code contained within the DNA is of multiple types. Some sequences within the DNA are recognized by regulatory factors and control how the biopolymer information is expressed. Some sequences encode structural attributes that contribute to the overall use of the biopolymer material. And some sequences encode the RNA or proteins that carry out functions within the cell. For simplicity, DNA is usually represented as an ordered string of the deoxynucleotides (e.g., GATTCTAGGA, (SEQ ID NO:1)), but that simple string reflects the full function of the molecule. The RNA copy of the DNA is also a chain of nucleotides (adenosine, uridine, cytidine, and guanosine being the major ones) (e.g., AUGGACCAUA (SEQ ID NO:2)). Some RNAs are translated into proteins, which are strings of amino acid building blocks.

There are 20 principal amino acid building blocks, and proteins are often represented simply by an ordered string of sequence letters (e.g., MRKLAGQPS (SEQ ID NO:3)). The function of proteins is not, however, fully contained within this simple string, since the building blocks can be modified in multiple ways within a cell. Nonetheless, the sequence of the amino acids is the primary contributor to the function of the protein.

The realm of bioinformatics is largely focused on trying to predict the function of genomic sequences. This work involves comparing the strings of information (genomic sequences), functional properties, and behavior of known and unknown entities, thereby providing a basis for predicting the similar function of sequences with similar properties. These methods, however, are not usually geared toward simultaneous analysis of a large number of sequences. Thus, it is difficult to get an overview of how all the unknown and known sequences relate to each other from these methods.

A number of multivariate analysis methods, including those geared toward data visualization and data mining, are available. In each case, a data object is represented as a high-dimensional vector, where the number of dimensions is equal to the number of independent attributes required to describe the data object.

For data strings, such as genome sequences, however, there are relatively few methods that have been applied to represent the information as a high-dimensional vector. One method creates a signature for protein sequences based on the occurrence of all possible amino acid dimers (or pairs of amino acids). See van Heel M., *A New Family of Powerful Multivariate Statistical Sequence Analysis Techniques*, 220 J. Mol Biol 877 –887 (1991). Application of this method with 20 amino acids resulted in a 20×20 or 400-dimensional representation for each protein for comparison using cluster analysis.

Another method also includes information about individual amino acids (composition) and descriptive information such as length of the sequence and pi (isoelectric point). These composite vectors were then used for searching data sets to identify similar sequences. See Hobohm U. and Sander C., *A Sequence Property Approach to Searching Protein Databases*, 251 J. Mol. Biol. 390–399 (1995).

While the goal in creating vectors in the above methods was to create a surrogate for functional information in the proteins, these methods do not provide sufficient discrimination to represent the subtle differences between most genomic sequences.

A different approach for mathematical representation of sequences for multivariate analysis is to use an ordination method. See Higgins D. G., *Sequence Ordinations: a Multivariate Analysis Approach to Analyzing Large Sequence Data Sets*, 8 Comput. Appl. Biosci. 15–22 (1992). Such a method uses the square root of the percentage difference between two sequences as a Euclidean distance. Then, each protein is represented within a distance matrix derived from all comparisons. The usefulness of percentage differences as a distance measure, however, is limited to closely related sequences. U.S. Pat. No. 5,930,784 to Hendrickson, issued Jul. 27, 1999, provides an example of using geometric distances among all items in a data set for data mining.

These methods are quite limited, however, when comparing proteins with limited similarity or when analyzing a large number of proteins simultaneously.

SUMMARY OF THE INVENTION

Systems and methods consistent with the present invention generate a high-dimensional vector representation of a sequence string of units in a data set, including a plurality of sequence strings, by operations for dividing each of respective sequence strings into blocks of three units or more to create a vocabulary of blocks, defining a respective vector axis to correspond to blocks in the vocabulary, determining for each vector axis whether a string includes a block corresponding to the respective vector axis, and creating a high-dimensional vector based on the determining.

Methods consistent with the present invention generate a high-dimensional vector representation of an item of biopolymer material in a data set including a plurality of items of biopolymer material by selecting predefined domains of the plurality of items of biopolymer materials, defining a respective vector axis to correspond to the selected domains, determining for each vector axis whether an item of biopolymer material includes a domain corresponding to the respective vector axis, and creating a high-dimensional vector based on the determining.

Methods consistent with the present invention generate a high-dimensional vector representation of an item of biopolymer material in a data set including a plurality of items of biopolymer material, by defining each item of biopolymer material in the data set as a surface using descriptors of at least one of structure and function, defining a respective vector axis to correspond to descriptors, determining for each vector axis whether an item of biopolymer material includes a descriptor corresponding to the respective vector axis, and creating a high-dimensional vector based on the determining.

Methods consistent with the present invention generate a high-dimensional vector representation of an item of biopolymer material in a data set including a plurality of items of biopolymer material by comparing information regarding each biopolymer material of the plurality to information regarding each other biopolymer material to provide a respective result, arranging the results in a square matrix indexed by the plurality of items of biopolymer materials, creating a high-dimensional vector for an item of biopolymer material based on a row or column of the matrix, and creating a distance matrix based on the high-dimensional vector.

An apparatus consistent with the present invention generates a high-dimensional vector representation of an item of biopolymer material in a data set including a plurality of items of biopolymer material and includes at least one memory having program instructions, and at least one processor configured to execute the program instructions to perform the operations to generate the high-dimensional vector.

A computer-readable medium consistent with present invention contains instructions for controlling a computer system to generate a high-dimensional vector representation of an item of biopolymer material in a data set including a plurality of items of biopolymer material.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the implementations of the invention and together with the description, serve to explain the principles of the invention.

DETAILED DESCRIPTION OF THE INVENTION

Reference will now be made in detail to the construction and operation of an implementation of the present invention which is illustrated in the accompanying drawings. The present invention is not limited to this implementation but it may be realized by other implementations.

A. Overview

Methods and systems consistent with the present invention extract attributes from sequence strings and from information representing biopolymer materials. Sequence strings are useful to provide an abstract representation of a complex object. In the biosciences, sequence strings are used to represent biopolymer materials, which are macromolecules found within a living thing, such as proteins, nucleic acids (such as DNA or RNA), polysaccharides, and mulitprotein and other complexes. Using sequence strings, bioscientists are provided with a common language to compare the features of different biopolymer materials.

Nevertheless, sequence strings of biopolymer materials are difficult to analyze, especially in large numbers. For example, most people can only remember seven units of unrelated information at a time (such as a seven-digit phone number) and sequence strings can be much longer than seven digits. With the need for analysis of a large number of biopolymer materials, analysis by a person is impractical. Fortunately, computer processing can make such analysis easier.

Computer processing, however, must be able to understand the sequence string. Particularly, when one seeks to view a relationship between numerous objects having numerous attributes, the computer must be able to define the attributes of the objects. Accordingly, methods and systems consistent with the present invention provides a computer with understandable attributes of biopolymers and other objects.

Using such methods and systems, relationships of information corresponding to structures such as biopolymer materials can be examined simultaneously. Thus, a user can discover relationships of biopolymer material not based on linear alignments but rather on overall characteristic relationships. Such relationships could be used to create, for example, a cure for a particular disease while eliminating side-effects.

B. Architecture

Figure 1:
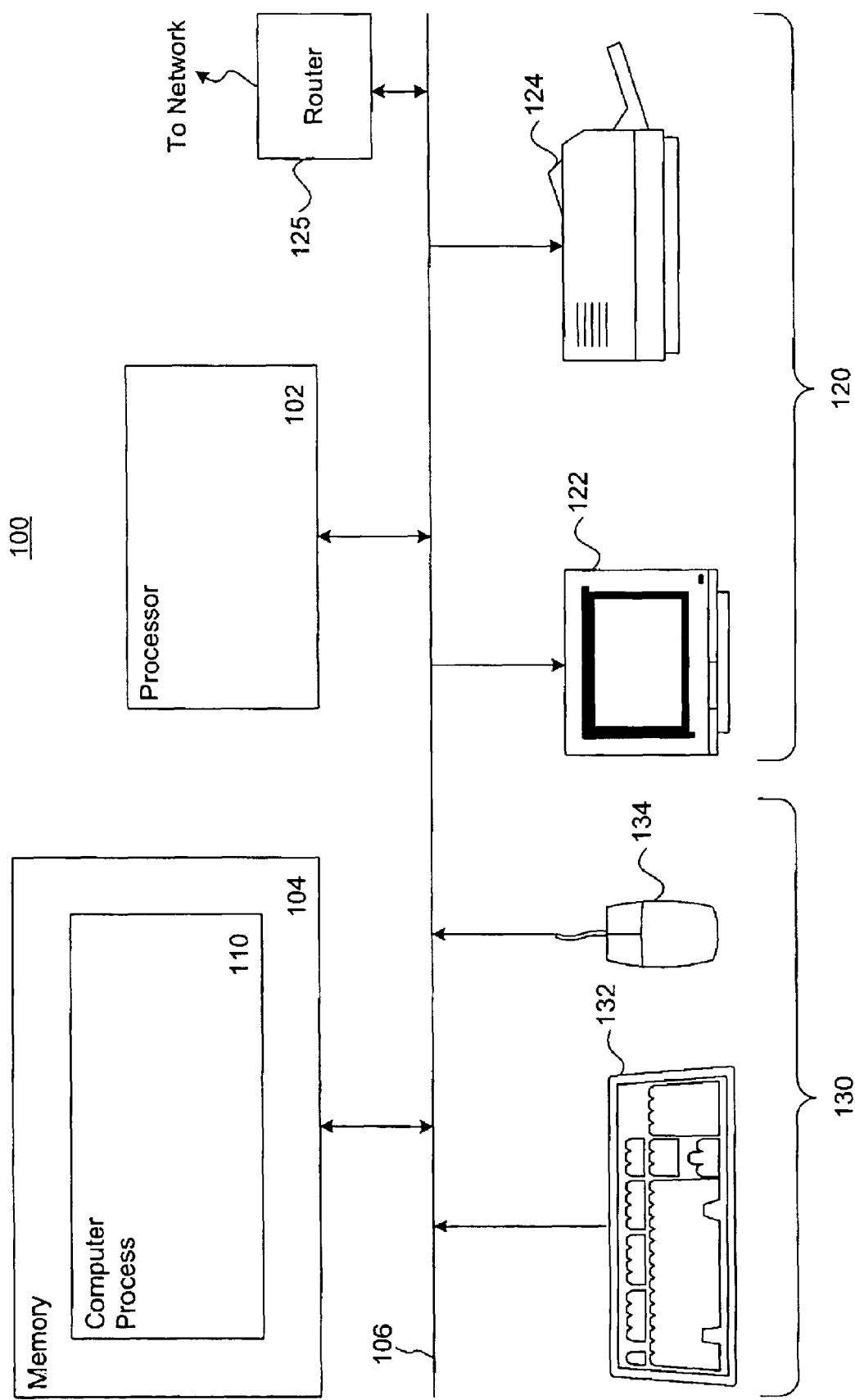
FIG. 1 is a diagram of an exemplary computing system with which the present invention may be implemented.

FIG. 1 is a diagram of an exemplary computer system 100 that can carry out processes consistent with the present invention. Computer system 100 includes a processor 102 and a memory 104 coupled to processor 102 through a bus 106. Processor 102 fetches computer instructions from memory 104 and executes those instructions. Processor 102 also (1) reads data from and writes data to memory 104, (2) sends data and control signals through bus 106 to one or more computer output devices 120, (3) receives data and control signals through bus 106 from one or more computer input devices 130 in accordance with the computer instructions, and (4) transmits and receives data through bus 106 and router 125 to a network.

Memory 104 can include any type of computer memory including, without limitation, random access memory (RAM), read-only memory (ROM), storage devices that include storage media such as magnetic and/or optical disks, and network-based memory devices. Memory 104 includes a computer process 110, such as a Web browser or Web server software or a process consistent with the present invention. A computer process includes a collection of computer instructions and data that collectively define a task performed by computer system 100.

Computer output devices 120 can include any type of computer output device, such as a printer 124, and display 122 such as a cathode ray tube (CRT), a light-emitting diode (LED) display, or a liquid crystal display (LCD). Display 122 preferably displays the graphical and textual information received from a computer process. Each of computer output devices 120 receives from processor 102 control signals and data and, in response to such control signals, displays data.

User input devices 130 can include any type of user input device such as a keyboard 132, or keypad, or a pointing device, such as an electronic mouse 134, a trackball, a lightpen, a touch-sensitive pad, a digitizing tablet, thumb wheels, or a joystick. Each of user input devices 130 is used to generate signals in response to physical manipulation by a user and transmits those signals through bus 106.

C. Architectural Operation

Figure 2:
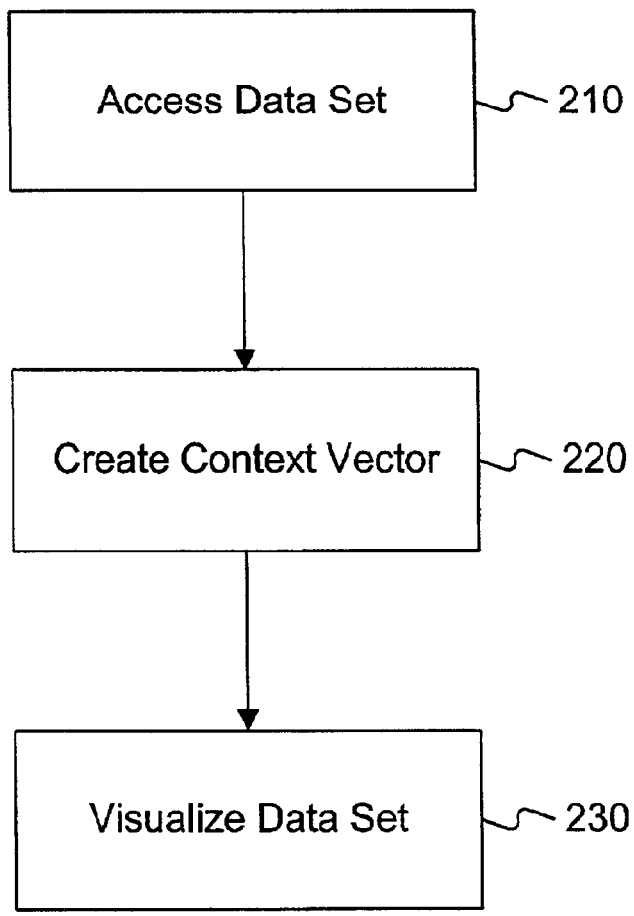
FIG. 2 is a flow chart of steps used to visualize a data set of biopolymer material consistent with the present invention.

FIG. 2 illustrates steps of a computer process used to visualize a data set representing biopolymer material, e.g. a protein data set. First, the data set is accessed (step 210). A context vector is created for each of the biopolymer materials, e.g. proteins, in the data set (step 220). The context vector will be of a very high-dimension, so as to represent many attributes of the protein. The context vectors are used to visualize the data set to find related or unrelated attributes of the proteins (step 230).

1. Sequence Data

Figure 3:
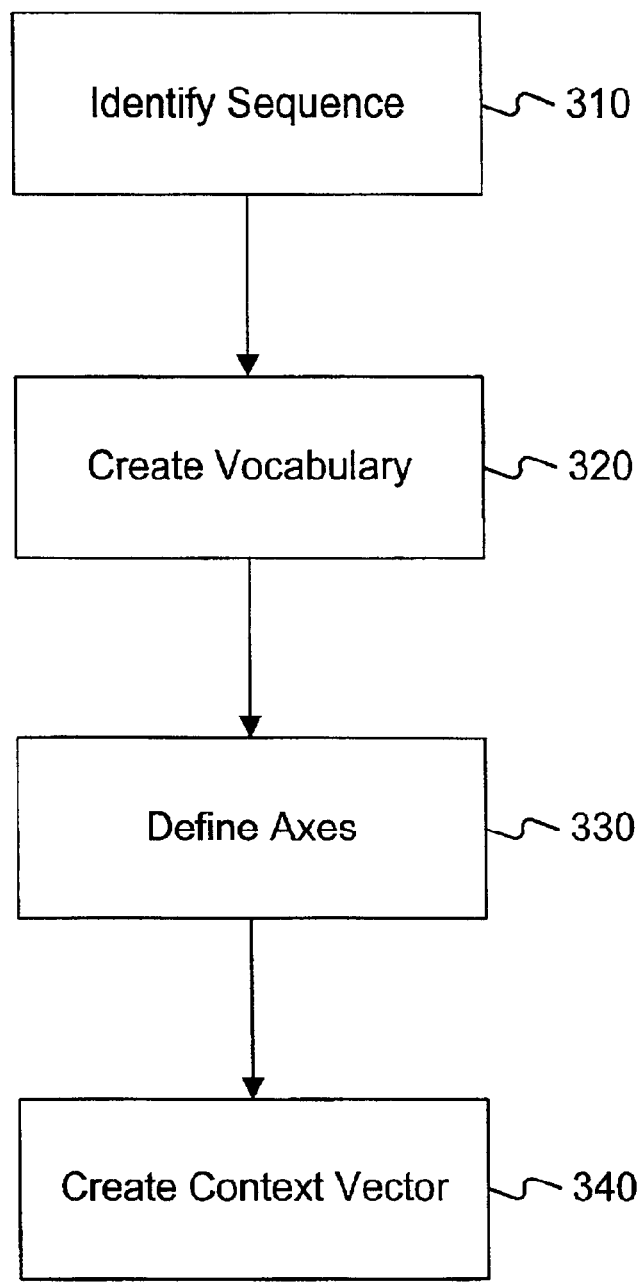
FIG. 3 is a flow chart of steps of an implementation of a method for creating context vectors for sequence strings.

A first method for creating context vectors for biopolymer material uses sequence data and is shown in FIG. 3.

In this method, each protein in the data set is identified as a respective series of sequence letters corresponding to the amino acid building blocks of the protein. The series of sequence letters lacks ascertainable attributes (step 310). Therefore, is it necessary to use special processing to determine the attributes of the sequence data.

To determine attributes of the sequence data, a vocabulary is created to define attributes of the protein (step 320). Generally, the sequence data is treated as a text document consisting of a number of words, or n-grams. For example, if a series of sequence letters representing a protein is ABCDEF, where each letter is an amino acid, then the protein could be represented as consisting of the n-gram words ABC and DEF, where n equals three. The selection of the length of the n-gram word is important. If a word consists of two or fewer units of the sequence string, such as amino acids, then each word will not convey much information. On the other hand, if words are too long then every word would be unique and, thus, no comparisons of common attributes would be possible. In one implementation, n-grams words of three units (three-mers) and n-gram words of four units (four-mers) provide enough discrimination for proteins, which have a 20-letter alphabet, and create a vocabulary of reasonable size.

Nevertheless, the use of one-mers, two-mers, and large n-mers, is within the scope of the invention.

Once a proper word length is determined, the protein sequence is represented by the words. However, protein functionality is often determined by its distinct stretches of its amino acids. Thus, arbitrarily breaking the protein into words might not generate the particular strain of amino acids that best define the protein's function. In order to not disturb the particular strain of amino acids, the protein is preferably divided into a set of overlapping words. For example, the sequence ABCDEF would be represented as ABC, BCD, CDE, and DEF using three-mers instead of simply using ABC and DEF.

Using the process of dividing each series of sequence letters into blocks of overlapping amino acids, a vocabulary of n-gram words is created that indicate the attributes of each of the proteins in the data set.

Referring to FIG. 3, each of the words of the vocabulary is set to a respective axis in a high-dimensional space (step 330). Because of the 20-letter alphabet for proteins, using three-mers will provide a $20^3$-dimensional space as a maximum. A large vocabulary, however, can create problems, because, for example, processing the vocabulary will require more computational power. Therefore, the vocabulary, and thus the high-dimensional space, is preferably reduced.

For example, statistical analysis can define the limited number of n-gram words that are most likely to convey information. Such statistical analysis can draw upon existing statistical analysis for natural language documents. For example, in U.S. patent application Ser. No. 08/713,313, entitled "System for Information Discovery," words that are too frequent or too infrequent in the data set can be ignored. Also, statistical analysis can define the most non-random words in the data set and use these words as the vocabulary. Other statistical analysis could select the most appropriate words for the vocabulary.

In conjunction with or instead of the statistical analysis, the vocabulary can be reduced by utilizing certain n-gram words as equivalent. Proteins with similar function can diverge through evolution. In other words, evolutionary changes that involve conservative amino acids substitutions (replacing an amino acid with one of similar chemical character) often occur. Therefore, treating n-gram words representing amino acids having a similar chemical character as identical will further reduce the vocabulary without deleterious effects on the analysis. For example, the n-gram word GGE (glycine-glycine-glutamic acid) is quite different from the n-gram word GGD (glycine-glycine-aspartic acid). However, with a conservative amino acid substitution, the n-gram word for both will be equivalent, with the proteins having the different n-gram words being viewed as more similar. To reduce the size of very large vocabularies, even more latitude can be incorporated into the substitutions, for example, using a single letter for all polar amino acids. As the vocabulary is reduced using any of the above methods, longer n-gram words may be used. Thereby, comparisons of longer sequence fragments can be made.

After the vocabulary is created, a high-dimensional context vector is created for each sequence string, e.g. protein sequence, in the data set (step 340). To create the context vector, the n-gram words of each sequence string are compared to the vocabulary. In a binary scheme, the presence of an n-gram word will be used to place the magnitude of the context vector along the corresponding axis of the word in the high-dimensional space at a predetermined amount. Alternatively, the number of occurrences of an n-gram word in the protein will be used to increase a magnitude of the context vector along the corresponding axis of the word in the high-dimensional space in proportion to the number of occurrences. The absence of a word will result in a zero value for the corresponding axis of the word in the high-dimensional space. Thereby, a context vector for each protein is the data set is created.

The use of n-gram words to create context vectors can also be used for sequences representing things other than protein. For example, nucleotide sequences have an alphabet of only four letters (G, A, T, C). When the alphabet is reduced, the word length of the n-gram can be increased.

2. Predefined Domains

A second method for creating context vectors for biopolymer material uses predefined domains to define the attributes of the biopolymer material.

Generally speaking, proteins have evolved from a set of building blocks with each protein arising from a different combination of these building blocks. In proteins, building blocks are known as motifs, and represent structural or functional domains. All proteins are built from the same sets of motifs. Current research has identified approximately 5000 motifs so far.

Figure 4:
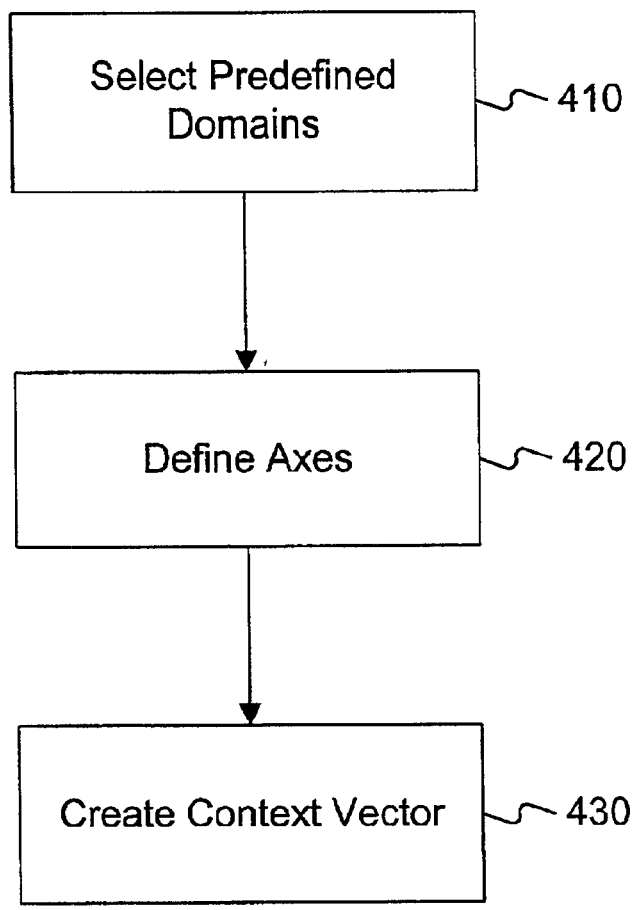
FIG. 4 is a flow chart of steps of an implementation of a method for creating context vectors for biopolymer materials utilizing predefined domains.

In this method, predefined domains of interest in the protein data set, such as motifs, are selected (see FIG. 4, step 410). For example, a user could select a file including motif definitions from a public domain set, such as PROSITE (available at various locations including www.expasy.ch/prosite), or could select any available file of motif definitions including a user-defined file. Because each motif is designated by all the combinations of sequences that could constitute that motif, each occurrence of the motif is designated with the same identifier. Thus, the method can account for degeneration of motifs. To reduce the number of selected motifs, combinations of motifs could be combined as a single motif. One method of combining motifs would be to treat the motifs as sequence letters and build n-gram words from contiguous structural attributes of the protein, as described above in connection with FIG. 3. Also, motifs can be combined based on their order of occurrence in the sequence.

Next, each of the selected predefined domains, e.g. motifs, is set to a respective axis in a high-dimensional space (step 420). After the axes are defined, a high-dimensional context vector is created for each protein in the data set (step 430). This is accomplished, for example, by determining the motifs of each protein. In a binary scheme, the presence of a motif will be used to place the magnitude of the context vector along the corresponding axis of the motif in the high-dimensional space at a predetermined amount. Alternatively, the number of occurrences of a motif in the protein will be used to increase a magnitude of the context vector along the corresponding axis of the motif in the high-dimensional space in proportion to the number of occurrences. Also, the methods for defining the magnitudes of axes could be combined, with motifs that indicate basic functionality represented as binary, and motifs whose functions depend on a number of occurrences represented in proportion to the number of occurrences. The absence of a motif will result in a zero value for the corresponding axis of the motif in the high-dimensional space. Thereby, a context vector for each protein is the data set is created.

Since the resulting vectors can produce a sparse matrix, it may be necessary to couple the values representing motifs with other values, such as n-grams frequency. For example, the occurrence of n-grams can represent additional dimensions in the context vector (as described for step 420). Alternatively, an association matrix can be built showing the probability of co-occurrence of each n-gram with each motif. Most n-grams will have some probability of co-occurring with each motif, albeit small in some cases. The weight given each motif along its respective axis in the high-dimensional context vector can then be assigned by the sum of probabilities for each n-gram in that sequence having co-occurred with that motif.

3. Geometric Shape

Figure 5:
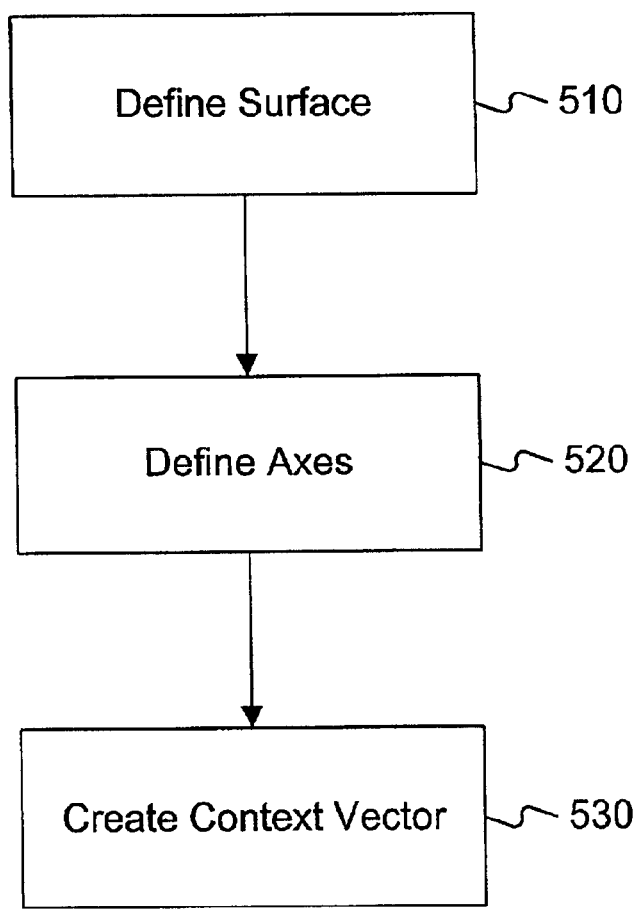
FIG. 5 is a flow chart of steps of an implementation of a method for creating context vectors for biopolymer materials utilizing a geometric shape.

Referring to FIG. 5, another method for creating context vectors for biopolymer material will be described. In this method, the protein can be considered a geometric shape, where the complex characteristics and properties of that shape describe the protein function, instead of using motifs to define the entire protein structure. First, a collection of descriptors of characteristics and properties describes each protein in a manner analogous to that for motifs (step 510). Spline functions generate the surface by representing characteristics and features as variables. The descriptors are then collected for all proteins in the data set and each descriptor is defined as an axis for the high-dimensional context vector (step 520). The context vector is created for each protein (step 530). In a binary approach, the value along each axis is set to either one if the descriptor is present or zero if absent. Like predefined domains, the value along each axis could alternatively be scaled by the number of occurrences for each descriptor.

4. Non-Geometric Indication

Figure 6:
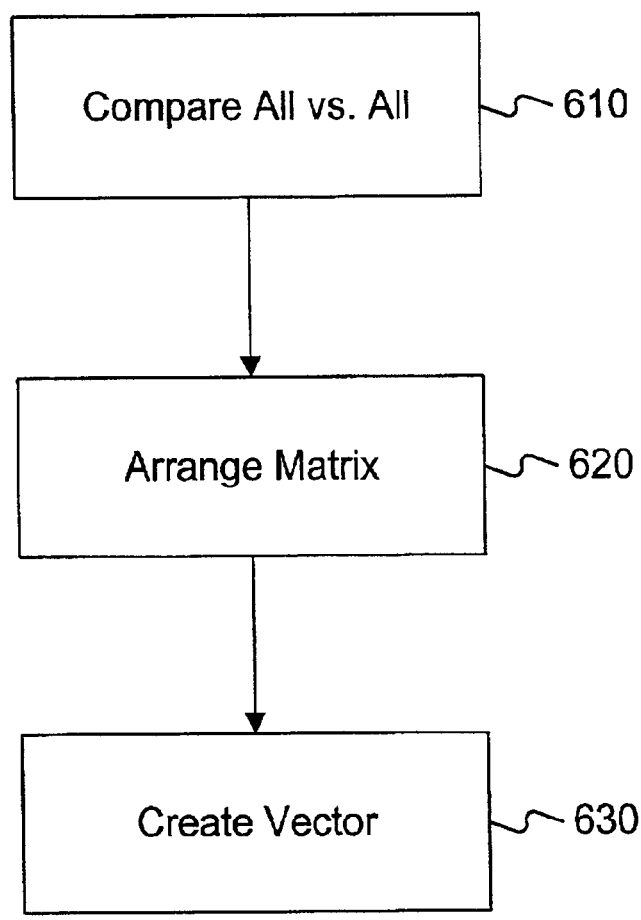
FIG. 6 is a flow chart of steps of an implementation of a method for creating context vectors for biopolymer materials utilizing a non-geometric indication of the biopolymer material.

FIG. 6 is a flow chart of another method for creating context vectors corresponding to biopolymer material using an indirect, relative, and non-geometric indication of the structure or function of the biopolymer material, rather than an indicator of the actual structure or portion thereof (by, e.g., using n-gram words, motifs, or surfaces).

A common method used for analysis of biopolymer material, e.g., protein, involves comparing each protein's structure to a data set of proteins to determine each protein's similarity to each of the other proteins. One conventional method, the Basic Local Alignment Search Tool (BLAST), provides a list of proteins from the data set rank ordered by expect values. Various entities provide BLAST algorithms including www3.ncbi.nlm.nih.gov/BLAST. The BLAST method provides a probability score when comparing one sequence against another. The score is usually expressed as the 'expectation' that in comparing the test sequence against a number of other sequences a match would have been found, e.g., a probability score of $1 \times 10^{-180}$ would say that there was very little expectation to have found the match by chance and thus the two sequences must be related. A score of close to one indicates that the match would have been expected by chance, i.e., the homology is very weak. To provide the probability score, BLAST uses a heuristic algorithm that seeks local as opposed to global alignments and is therefore able to detect relationships among sequences which share only isolated regions of similarity. In other words, the matches themselves are based on finding regions of similarity and, in the case of proteins, account for the fact that some amino acids could behave similarly at a given position. Thus, overall the BLAST method gives a very good picture of similarity and can be used to provide a non-geometric distance measure.

Specifically, BLAST segments a sequence string and searches for short regions that are identical. Each of these regions can serve as a nucleus for finding additional similarities, leading to an alignment between the sequences. The BLAST family of algorithms includes Gapped BLAST, which allows deletions and insertions in the alignments that are determined and provides scores potentially more reflective of biological relationships, and Position-Specific Iterated BLAST (PSI-BLAST), which derives initial BLAST scores and then uses those results to look for more distantly related sequences.

BLAST and the multitude of other methods for finding relationships (e.g., FASTA and Smith-Waterman) are able to find complex similarities including gaps between related regions.

When a large number of proteins are being analyzed, the list of output results can be voluminous and difficult to analyze, especially in a BLAST all-against-all experiment, where each item of biopolymer material, e.g. protein, from a user-identified set is compared to every other item in the set.

To create context vectors and, thus, more efficiently analyze a data set of a large number of items of biopolymer material, an all-against-all experiment is performed for all of the biopolymer material in the data set using a method that determines a relationship between proteins (step 610). One such method determines a probability score based on whether mere chance can explain the similarity in composition of the protein.

Figure 7:
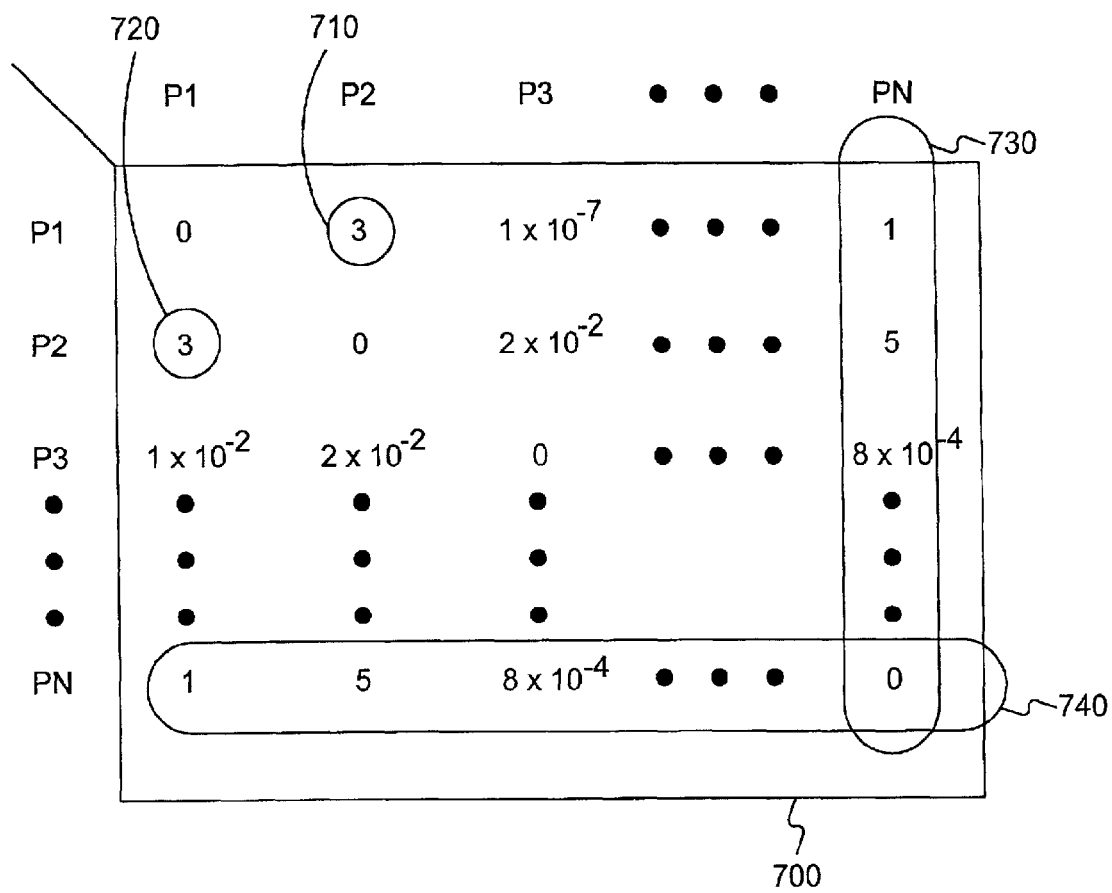
FIG. 7 is an illustration of a square matrix created in the method of FIG. 6.

The list output of the all-against-all experiment is read by a computer software routine that identifies the expect score for each comparison and arranges those as a square matrix in an electronic data file (step 620). An exemplary square matrix 700 representing a protein data set is shown in FIG. 7. Each protein indexes a respective row and a respective column of the matrix, so as to compare each protein with all other proteins. The values of the cells within the matrix are then populated to indicate how related the proteins are, that is, the expect score from the all-against-all experiment. In FIG. 7, illustrative circles 710 and 720 show that when protein P1 was compared to protein P2, an expect value of 3 was produced. Alternatively, similarity values could populate the matrix, where the similarity score would equal 1-expect score.

Once the matrix is populated, the rows or columns of the matrix are used to create a context vector for each protein in the data set (step 630). In one aspect of this implementation, this step is accomplished by considering an entire row or column as a vector. In other words, the vector for each of the N objects or proteins to be visualized, has N attributes. The i-th attribute is a comparison measurement between the i-th protein in the data set and the object protein. In FIG. 7, a context vector for the object protein PN would be (1, 5, $8 \times 10^{-4}$, . . . 0), as shown by illustrative oval 730 or oval 740. All of the context vectors constitutes an object attribute matrix.

Where the method for deriving relationship of one protein to another provides additional information, that information can be appended to the matrix and then defined as categorical, numeric, textual, or sequence data where the data set is visualized. For example, PSI-BLAST can provide information on how many iterations were required to identify the protein as being related.

In another aspect of this implementation, the values of the matrix can be adjusted to eliminate distortions created by the similarity determination method. The adjustment can occur at any time prior to population of the matrix, as the matrix is populated, after the matrix is populated, or after the context vectors are created. For example, a BLAST score above a predetermined value is truncated to the predetermined value to eliminate the distortion of relationships that occurs with poor similarity, as a high BLAST score indicates low similarity. Also, a predetermined minimum acceptable BLAST score can be substituted for scores below the predetermined minimum acceptable BLAST score, so as to control the relationships defined by very high homology by accounting for rounding errors in the BLAST routine that result in zero expectation values. Similarly, the scale for the similarity can be adjusted, for example, by taking the log of the expect score, which can provide greater weight to the lower expect values.

Once context vectors are provided, the context vectors are projected onto a two- or three-dimensional viewing area (step 230 of FIG. 2). For example, the context vectors are used to create a distance matrix. Clustering may then determine a centroid for a subset of proteins, and then the clusters and objects, e.g. proteins, are projected onto the two- or three-dimensional viewing area. Previously discussed U.S. patent application Ser. No. 09/408,716, entitled DATA PROCESSING, ANALYSIS, AND VISUALIZATION SYSTEM FOR USE WITH DISPARATE DATA TYPES, describes one method of visualizing context vectors based on sequence data.

D. Conclusion

While there has been illustrated and described what are at present considered to be a preferred implementation and method of the present invention, it will be understood by those skilled in the art that various changes and modifications may be made, and equivalents may be substituted for elements thereof without departing from the true scope of the invention.

Modifications may be made to adapt a particular element, technique, or implementation to the teachings of the present invention without departing from the spirit of the invention. For example, any living material, from organism to microbe, could be represented using the context vectors of the present invention. Further, the present invention is not limited to the biosciences, and any material or energy could also be represented.

Also, the foregoing description is based on a client-server architecture, but those skilled in the art will recognize that a peer-to-peer architecture may be used consistent with the invention. Moreover, although the described implementation includes software, the invention may be implemented as a combination of hardware and software or in hardware alone. Additionally, although aspects of the present invention are described as being stored in memory, one skilled in the art will appreciate that these aspects can also be stored on other types of computer-readable media, such as secondary storage devices, like hard disks, floppy disks, or CD-ROM; a carrier wave from the Internet; or other forms of RAM or ROM.

Therefore, it is intended that this invention not be limited to the particular implementation and method disclosed herein, but that the invention include all implementations falling within the scope of the appended claims.

What is claimed is:

1. A method of visualizing comparison results for at least one of a plurality of biopolymer materials represented in a set of sequences, the method comprising:
   comparing a sequence of each biopolymer material to a sequence of each other biopolymer material to provide respective comparison results;
   arranging the comparison results in a square matrix indexed by the plurality of biopolymer materials;
   creating a high-dimensional context vector for at least one of the biopolymer materials based on a row or column of the square matrix; and
   projecting the context vector onto a two- or three-dimensional viewing area;
   thereby visualizing comparison results for at least one of a plurality of biopolymer materials represented in the set of sequence.

2. The method according to claim 1, wherein from each row or column of the square matrix, a respective high-dimensional context vector is created for each of the biopolymer materials based on the comparison results in the row or column.

3. The method according to claim 1, wherein the comparing uses a Basic Local Alignment Search Tool.

4. The method according to claim 1, wherein the comparing provides comparison results based on an expectation of a relation.

5. The method according to claim 1, wherein the biopolymer material is protein.

6. The method according to claim 1, wherein the biopolymer material is nucleic acid.

7. The method of claim 1, wherein the context vector is utilized for comparison of the biopolymer materials using cluster analysis.

8. The method of claim 1, wherein the context vector comprises a row or column of an object attribute matrix of comparison results.

9. An apparatus for visualizing comparison results for at least one of a plurality of biopolymer materials represented in a set of sequences, the apparatus comprising:
   at least one memory having program instructions,
   at least one computer output device for visualizing comparison results, and
   at least one processor configured to execute the program instructions to perform the operations of:
   comparing a sequence of each biopolymer material to a sequence of each other biopolymer material to provide respective comparison results;
   arranging the comparison results in a square matrix indexed by the plurality of biopolymer materials;
   creating a high-dimensional context vector for at least one of the biopolymer materials based on a row or column of the square matrix; and projecting the context vector onto a two- or three-dimensional viewing area, wherein the apparatus enables visualization of the comparison results for the respective biopolymer material.

10. A computer-readable medium containing instructions for controlling a computer system to perform a method for visualizing comparison results for at least one of a plurality of biopolymer materials represented in a set of sequences, the method comprising:

comparing a sequence of each biopolymer material to a sequence of each other biopolymer material to provide respective comparison results;

arranging the comparison results in a square matrix indexed by the plurality of biopolymer materials;

creating a high-dimensional context vector for at least one of the biopolymer materials based on a row or column of the square matrix; and projecting the context vector onto a two- or three-dimensional viewing area, wherein the method enables visualization of the comparison results for the respective biopolymer material.

* * * * *